United States Patent [19]

Brockett et al.

[11] Patent Number: 5,595,728
[45] Date of Patent: Jan. 21, 1997

[54] AMINO ACID β-LYASE ENZYME INHIBITORS AS DEODORANTS

[75] Inventors: Sue Brockett, Bethesda; Clifford O'Neal, Gaithersburg; Hermes van der Lee, Olney, all of Md.; Brian Rogers, South Boston, Mass.

[73] Assignee: The Gillette Company, Boston, Mass.

[21] Appl. No.: 985,851

[22] Filed: Dec. 4, 1992

Related U.S. Application Data

[63] Continuation of Ser. No. 824,886, Jan. 22, 1992, Pat. No. 5,213,791, which is a continuation of Ser. No. 418,876, Oct. 10, 1989, abandoned.

[51] Int. Cl.$^6$ .............................. A61K 7/32; A61K 7/34; A61K 7/38; A61K 9/12
[52] U.S. Cl. ............... 424/65; 424/DIG. 5; 424/47; 424/66; 424/68
[58] Field of Search .................................. 424/65

[56] References Cited

U.S. PATENT DOCUMENTS

| | | | |
|---|---|---|---|
| 4,089,942 | 5/1978 | Boré et al. | 424/47 |
| 5,213,791 | 5/1993 | Lyon et al. | 424/65 |

FOREIGN PATENT DOCUMENTS

| | | | |
|---|---|---|---|
| 348210 | 12/1967 | Russian Federation | 514/640 |
| 1446584 | 8/1976 | United Kingdom | 424/65 |

OTHER PUBLICATIONS

Sagarin, Cosmetics Science & Technology, 1957, pp. 717, 733 and 1202 to 1211.

*Primary Examiner*—Shelley A. Dodson
*Attorney, Agent, or Firm*—Burns, Doane, Swecker & Mathis, L.L.P.

[57] ABSTRACT

A deodorant composition comprising a body odor suppressing effective amount of an inhibitor of an amino acid β-lyase enzyme which catalyzes the formation of human body malodor in a dermatologically acceptable vehicle.

12 Claims, No Drawings

AMINO ACID β-LYASE ENZYME INHIBITORS AS DEODORANTS

This application is a continuation of application Ser. No. 07/824,886, filed Jan. 22, 1992, now U.S. Pat. No. 5,213,791 which is a continuation of application Ser. No. 07/418,876, filed Oct. 10, 1989, now abandoned.

BACKGROUND OF THE INVENTION

The eccrine and apocrine sweat glands are the structures of the human body responsible for sweat. The apocrine glands become active at puberty and produce an odorless proteinaceous secretion. Axillary bacteria act on the apocrine secretions to produce the pungent odor known as axillary malodor. Prior to the current invention, the process by which bacteria produce malodor was unknown.

Current deodorants are generally of two types: odor maskers and germicides. Despite the many disclosures in the art pertaining to deodorant compositions, current products are not sufficient to suppress odor in a significant proportion of the population, particularly during periods of "stress." Thus, there remains a need for deodorant compositions and methods which are effective, safe and economical.

SUMMARY OF THE INVENTION

The present invention is a deodorant composition comprising a body odor suppressing effective amount of an inhibitor of an amino acid β-lyase enzyme in a dermatologically acceptable vehicle.

DETAILED DESCRIPTION OF THE INVENTION

The present invention includes novel compositions and a novel method of suppressing body odor by the topical application of a composition containing at least one inhibitor of an enzyme, amino acid β-lyase, which catalyzes the formation of human body malodor. These unique compositions act to suppress the formation of axillary malodor by inhibiting an amino acid β-lyase enzyme that is found to create axillary malodor within the bacterial cells. Such inhibitors include certain derivatized amino acids and hydroxylamines.

Deodorant compositions containing at least one of the inhibiting compounds in a body odor suppressing effective concentration will serve to suppress axillary malodor when applied to the underarm. As shown by the examples set forth below, these compositions significantly attenuate the body odors formed in the axilla.

Axillary malodor is generated by certain skin bacteria in the presence of apocrine secretion. Two strains of bacteria have been identified which produce axillary malodor when incubated with human apocrine secretions. These are certain *Staphylococccus* species and several Coryneform isolates. The conversion of apocrine precursor to axillary malodor occurs within the bacterial cells. Even extracts of bacteria cells are capable of converting the precursor to the malodor compound in an enzymatic process. The enzyme which promotes this conversion has been designated as the malodor-forming enzyme and is an amino acid β-lyase.

Production of human axillary malodor can be assayed from these strains of bacteria. One such assay is conducted by incubating bacteria ($10^9$/ml) for 30 minutes at 37° C. in a phosphate buffer at pH 6.8 with apocrine secretions collected from human axilla. The volatile malodor compound is then extracted into chloroform and smelled after spotting on filter paper. A similar assay can be conducted using malodor-forming enzyme in place of the bacteria.

The malodor-forming enzyme has been found to be an amino acid β-lyase which acts in the axilla to cleave amino acids with the general structure COOH—CH(NH$_2$)—CH$_2$—S—R where R is generally alkyl. The resulting volatile sulfur products are responsible for the pungent smell characteristic of human axillary odor.

The malodor forming enzyme contains the cofactor pyridoxal phosphate. Pyridoxal phosphate dependent enzymes are known to be inhibited by certain hydroxylamines and derivatized amino acids. The following groups of compounds were found to be inhibitors of the malodor-forming enzyme.

Group 1: Hydroxylamine and other compounds of the formula H$_2$N—O—CH(R)COOH where R is hydrogen; phenyl; or C$_1$–C$_8$ alkyl which is unsubstituted or substituted by a phenyl group, a hydroxy group, a carboxy group, a benzyloxy or benzyloxycarbonyl group, a halogen or an amino group.

Group 2: Amino acids containing a halogen at the β-carbon, such as β-chloroalanine and trifluoroalanine, with the formula NH$_2$—CH(—R)COOH where R is CR$^1$R$^2$R$^3$ where R$^1$ is a halogen and R$^2$ and R$^3$ are the same or different and are hydrogen, chlorine, fluorine, iodine, bromine, a phenyl group, or C$_1$–C$_8$ alkyl which is unsubstituted or substituted by a phenyl group, a hydroxy group, a carboxy group, a benzyloxy group, a benzyloxycarbonyl group or an amino group.

Group 3: α-Methyl amino acids of the formula NH$_2$—C(CH$_3$)(COOH)—CH$_2$—S—R where R is hydrogen, phenyl, C$_1$–C$_8$ alkyl which is unsubstituted or substituted by a phenyl group, a hydroxy group, a carboxy group, a benzyloxy or benzyloxycarbonyl group, a halogen or an amino group.

Group 4: Cycloserine and related cyclic amino acids of the formula:

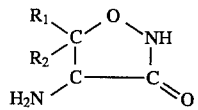

where R$_1$ and R$_2$ are hydrogen; phenyl; or C$_1$–C$_8$ alkyl which is unsubstituted or substituted by a phenyl group, a hydroxy group, a carboxy group, a benzyloxy or benzyloxycarbonyl group or an amino group.

Group 5: Pyridoxal phosphate derivatives of the formula:

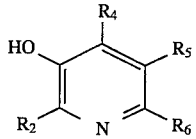

wherein

R$_2$ is amino, halogen, saturated or unsaturated alkyl which is unsubstituted or substituted with an amino group, an oxo group, halogen, or a carboxylic group;

R$_4$ is amino, halogen, saturated or unsaturated alkyl which is unsubstituted or substituted with hydroxyl, an oxo group, a carboxylic group, halogen, or an amino group;

R$_5$ is hydrogen, unsaturated or saturated alkyl which is unsubstituted or substituted with a carboxylic group, a hydroxyl group, halogen, an oxo group or a phosphate group; and $R_6$ is hydrogen, halogen or an amino group.

The above compounds block enzymatic formation of axillary malodor and therefore serve as deodorants.

Although deodorancy is the most important concern for the consumer of underarm products, many also choose a product with antiperspirant activity. Current antiperspirants, which are aluminum salts, also function as deodorants by virtue of their germicidal properties. Thus,. if desired, the deodorants of the present invention can be employed with the antiperspirant compounds well known in the art. In such formulations, the inhibitors of the malodor forming enzyme of the present invention can be incorporated into an antiperspirant formulation with the antiperspirant being employed in a perspiration reducing effective concentration.

The antiperspirant component used in the present invention may be any of those which contain aluminum, either alone or in combination with other materials such as zirconium. Typical aluminum salts, although not all-inclusive, include:

Aluminum chlorohydrate;
Aluminum sesquichlorohydrate;
Aluminum dichlorohydrate;
Aluminum chlorohydrex PG or PEG;
Aluminum sesquichlorohydrex PG or PEG;
Aluminum dichlorohydrex PG or PEG;
Aluminum zirconium trichlorohydrate;
Aluminum zirconium tetrachlorohydrate;
Aluminum zirconium tetrachlorohydrex PG or PEG;
Aluminum zirconium pentachlorohydrate;
Aluminum zirconium octachlorohydrate;
Aluminum zirconium trichlorohydrex-gly;
Aluminum zirconium tetrachlorohydrex-gly;
Aluminum zirconium pentachlorohydrex-gly;
Aluminum zirconium octachlorohydrex-gly;
Aluminum zirconium chloride;
Aluminum zirconium sulfate;
Potassium aluminum sulfate;
Sodium aluminum chlorohydroxylacetate;
Aluminum bromohydrate.

In general the active antiperspirant component should be present in the same amounts at which such materials are employed in prior art compositions. As a general rule, the antiperspirant composition should contain from about 5% to about 30%, preferably from about 10 to 25% of the active antiperspirant salt component.

In order to further illustrate the present invention and the advantages thereof, the following specific examples are given. It is understood that these examples are intended only to be illustrative without serving to limit the scope of the present invention.

EXAMPLES

Example 1

Evaluation of hydroxylamine and its derivatives.

As a representative of hydroxylamine derivatives, aminooxyacetic acid ($H_2N$—O—$CH_2$—COOH) was investigated. Aminooxyacetic acid was shown to inhibit in vitro malodor formation in the assay described above at concentrations from 0.1 to 10 µM in a pH 6.8 phosphate buffer. Inhibition was complete at concentrations over 3 µM. When tested for the ability to block malodor formation when whole bacterial cells were used in the malodor assay, the minimal concentration needed for complete inhibition was 100 µM. Aminooxyacetic acid at 0.11% by weight in water at neutral pH was found to be efficacious when tested clinically for deodorancy.

Further clinical trials were carried out to assess the deodorancy properties of the Group 1 compound aminooxyacetic acid (AOA). AOA at 1.1% by weight/volume at pH 7 in a vehicle of 50% propylene glycol/50% water outperformed triclosan, which was at 0.1% by weight/volume at self pH in the same vehicle. Triclosan is a germicide employed as an active ingredient in certain current underarm deodorants. The combination of AOA at 1.1% by weight/volume and triclosan at 0.1% by weight/volume at pH 7 in a vehicle of 50% propylene glycol/50% water outperformed triclosan at 0.1% by weight volume at self pH in the same vehicle. AOA at 2.2% by weight also outperformed triclosan at 0.1% by weight in a stick formulation. Finally, the combination of AOA at 1.1% by weight and the antiperspirant aluminum chlorohydrate at 20% by weight in a vehicle of 50% propylene glycol/50% water outperformed aluminum chlorohydrate at 20% by weight in the same vehicle.

Example 2

Evaluation of β-substituted amino acids.

Among the β-substituted amino acids, β-chloroalanine and trifluoroalanine were tested for their ability to inhibit malodor in vitro. Both inhibited activity; trifluoroalanine inhibited completely at concentrations over 50 µM and β-chloroalanine inhibited completely at concentrations over 10 µM. Both were tested in a pH 6.8 phosphate buffer. Both compounds were effective in the inhibition of malodor in the presence of whole bacterial cells at concentrations greater than 1 mM. Trifluoroalanine was tested in a deodorancy clinical trial and found to be efficacious at 0.14% in water.

Example 3

Evaluation of α-methyl amino acid derivatives.

The α-methyl derivative of S-benzyl cysteine inhibits the formation of malodor in vitro. This compound also inhibits malodor formation in whole cells and by isolated malodor-forming enzyme at levels over 1 mM in a pH 6.8 phosphate buffer.

Example 4

Evaluation of cycloserine and derivatives.

Cycloserine was tested in vitro against whole bacterial cells and malodor-forming enzyme for its ability to inhibit malodor formation, and was found to completely inhibit the formation of malodor in both systems at levels over 1 mM in a pH 6.8 phosphate buffer.

Example 5

Evaluation of pyridoxal and its derivatives.

Pyridoxal was tested in vitro against malodor-forming enzyme for its ability to inhibit the formation of malodor. It was effective in eliminating malodor at concentrations over 10 mM.

To prove that the inhibitors are suppressing malodor by enzyme inhibition rather than acting as germicides, several of the above compounds were tested for germicidal activity against axillary bacteria. Aminooxyacetic acid, trifluoroalanine, and L-cycloserine at concentrations up to 0.1M had no inhibitory effect on the growth of *Staphylococcus* cells in culture.

Formulations for Deodorant Use

The inhibitors of the present invention may be formulated for application to the skin employing any of the ingredients typically used in deodorant and antiperspirant formulations. The concentration of active ingredient employed in topical applications should be consistent with efficacy, economy and safety. The active inhibitors are efficacious within concentrations of about 1 micromolar to about 2 molar. The preferred range is about 1–200 millimolar. This constitutes a weight percent of about 0.01% to 3% as the preferred range of active ingredient.

If desired, the inhibitor of the present invention can also be employed in combination with an antiperspirant. In such case, the inhibitor is merely added to the standard formulation for the antiperspirant composition in the same concentrations as set forth above.

Examples of formulations are given below:

1. Deodorant Stick

|  | % |
| --- | --- |
| propylene glycol | 78 |
| sodium stearate C-1 | 7.9 |
| fragrance | 0.1 |
| 9 wt. % aminooxyacetic acid in water at neutral pH | 14 |

Procedure: Mix propylene glycol and sodium stearate C-1 at room temperature and stir. Increase the temperature to about 70° C. and continue agitation to obtain a clear and uniform solution. Add the aminooxyacetic acid solution. Lower the temperature to 55° C. and add the fragrance. Pour into molds and cool to room temperature.

2. Deodorant Roll-on Emulsion

|  | % |
| --- | --- |
| hydrogenated palm oil glycerides and sodium cetyl sulfate | 3.0 |
| steareth-7 | 1.0 |
| octyldodecanol | 4.0 |
| glyceryl laurate | 2.0 |
| octyl palmitate | 4.0 |
| dimethicone | 1.0 |
| propylparaben | 0.1 |
| methylparaben | 0.2 |
| imidazolidinyl urea | 0.3 |
| glycerin | 5.0 |
| allantoin | 0.5 |
| PEG-35 lanolin | 0.5 |
| fragrance | 0.3 |
| 2 wt. % aminooxyacetic acid in water at neutral pH | 78.1 |

Procedure: Mix and stir the ingredients except the fragrance at 80° C. Decrease the temperature to 40° C. and add the fragrance. Decrease the temperature to room temperature.

3. Aerosol Deodorant

|  | % |
| --- | --- |
| zinc phenolsulfonate | 1.7 |
| quaternium 18 hectorite | 1.0 |
| dioctyl succinate | 10.0 |
| SDA 40 ethanol, anhydrous | 20.0 |
| fragrance | 0.1 |
| 10 wt. % aminooxyacetic acid in water at neutral pH | 10.0 |

3. Aerosol Deodorant -continued

|  | % |
| --- | --- |
| propellent | 57.2 |

Procedure: Dissolve all ingredients in the alcohol, add the propellent, and cold or pressure fill.

4. Roll-on Antiperspirant and Deodorant

|  | % |
| --- | --- |
| PPG-15 stearyl ether | 4.0 |
| steareth-21 | 0.6 |
| steareth-2 | 2.6 |
| aluminum zirconium pentachlorohydrate, 10:1 (a 25% solution) | 32.0 |
| fragrance | 0.1 |
| 1.8 wt. % aminooxyacetic acid in water at neutral pH | 60.7 |

Mix all the ingredients except the fragrance at 70° C. with agitation. Add the fragrance at 45° C. Stir and cool to room temperature.

5. Aerosol Antiperspirant and Deodorant

|  | % |
| --- | --- |
| aminooxyacetic acid | 1.0 |
| isopropyl myristate | 13.4 |
| aluminum chlorohydrate | 10.0 |
| quaternium-18 hectorite | 0.8 |
| SDA 40 ethanol, anhydrous | 0.8 |
| fragrance | 0.1 |
| propellent | 73.9 |

Procedure: Mix the isopropyl myristate and quaternium-18 hectorite together for 30 min with an Eppenbach Homomixer. Add aluminum chlorohydrate and mix 15 min. Add the aminooxyacetic acid and SDA 40 and mix 10 min. Homogenize the suspension using a Manton-Gaulin homogenizer set at 6000 psi. Add fragrance and mix on a Hobart Mixer set at moderate speed. Mix 10 min. Charge with propellent.

6. Stick Antiperspirant and Deodorant

|  | % |
| --- | --- |
| aluminum chlorohydrate | 16.0 |
| SDA 40 ethanol, anhydrous | 30.0 |
| sorbitol, 70% | 3.0 |
| sodium stearate C-1 | 5.0 |
| sodium ceteth-13 carboxylate | 3.0 |
| stearyl alcohol | 1.0 |
| cyclomethicone | 15.0 |
| fragrance | 0.1 |
| 4.1 wt. % aminooxyacetic acid in water at neutral pH | 26.9 |

Procedure: Mix the aluminum chlorohydrate, SDA 40 ethanol and the aminooxyacetic acid and heat to 65° C. Add sorbitol and then sodium stearate C-1 and sodium ceteth-13 carboxylate, and mix until a complete solution is obtained. Add the remaining ingredients and mix for 5 min. Cool to 50° C. and add to containers.

While the invention has been described in terms of various embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. A deodorant composition comprising a body odor suppressing effective amount of an inhibitor of an amino acid β-lyase enzyme containing the cofactor pyridoxal phosphate and which cleaves amino acids with the structure COOH—CH(NH$_2$)—CH$_2$—S—R where R is alkyl, in a dermatologically acceptable vehicle.

2. A deodorant composition comprising a body odor suppressing effective amount of an inhibitor of an amino acid β-lyase enzyme containing the cofactor pyridoxal phosphate and which cleaves amino acids with the structure COOH—CH(NH$_2$)—CH$_2$—S—R where R is alkyl, wherein the inhibitor is a compound of the formula

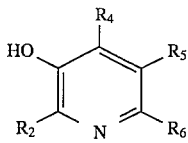

wherein
- R$_2$ is amino, halogen, saturated or unsaturated alkyl which is unsubstituted or substituted with an amino group, an oxo group, halogen, or a carboxylic group;
- R$_4$ is amino, halogen, saturated or unsaturated alkyl which is unsubstituted or substituted with hydroxyl, an oxo group, a carboxylic group, halogen, or an amino group;
- R$_5$ is hydrogen, unsaturated or saturated alkyl which is unsubstituted or substituted with a carboxylic group, a hydroxyl group, halogen, an oxo group or a phosphate group; and
- R$_6$ is hydrogen, halogen or an amino group, in a dermatologically acceptable vehicle.

3. The composition of claim 1 wherein the inhibitor is present at a concentration of at least 0.01% by weight.

4. The composition of claim 1 wherein the inhibitor is present at a concentration of about 1 micromolar to about 500 millimolar.

5. The deodorant composition of claim 1 wherein the inhibitor is a compound of the formula

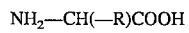

where R is CR$^1$R$^2$R$^3$ where R$^1$ is a halogen and R$^2$ and R$^3$ are the same or different and are hydrogen, chlorine, fluorine, iodine, bromine, a phenyl group, or C$_1$–C$_8$ alkyl which is unsubstituted or substituted by a phenyl group, a hydroxy group, a carboxy group, a benzyloxy group, a benzyloxycarbonyl group or an amino group.

6. The deodorant composition of claim 1 wherein the inhibitor is a compound of the formula

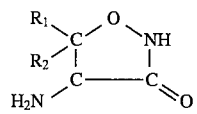

where R$_1$ and R$_2$ are hydrogen, phenyl, or C$_1$–C$_8$ alkyl which is unsubstituted or substituted by a phenyl group, a hydroxy group, a carboxy group, a benzyloxy or benzyloxycarbonyl group or an amino group.

7. The composition of claim 1, 2, 5 or 6, wherein the concentration of inhibitor is about 1–200 millimolar.

8. The composition of claim 1, 2, 5 or 6, further comprising an antiperspirant salt.

9. A method of suppressing body odor comprising the application to skin of the composition of claim 1, 2, 5 or 6.

10. The composition of claim 2, wherein the inhibitor is present at a concentration of at least 0.01% by weight.

11. The composition of claim 2, wherein the inhibitor is present at a concentration of about 1 micromolar to about 500 millimolar.

12. The composition of claim 2, wherein the inhibitor is pyridoxal.

* * * * *

UNITED STATES PATENT AND TRADEMARK OFFICE
CERTIFICATE OF CORRECTION

PATENT NO. : 5,595,728
DATED : Jan. 21, 1997
INVENTOR(S) : BROCKETT et al

It is certified that error appears in the above-indentified patent and that said Letters Patent is hereby corrected as shown below:

Please correct the cover page of the patent as follows:

At [45], before "Jan. 21, 1997" please insert -- * --.

Before [21], please insert:

-- [*] Notice: The portion of the term of this patent subsequent to May 25, 2010, has been disclaimed. --

At column 3, line 8, after "Thus," please delete -- . --.

Signed and Sealed this

Eighteenth Day of November 1997

Attest:

BRUCE LEHMAN

*Attesting Officer*   Commissioner of Patents and Trademarks